United States Patent [19]
Marchand et al.

[11] Patent Number: 5,674,455
[45] Date of Patent: Oct. 7, 1997

[54] AXIALLY COMPRESSIBLE DEVICE FOR CHROMATOGRAPHY

[75] Inventors: Claude Marchand, Hölstein; Charles Baur, Sanges-St. Aubin, both of Switzerland

[73] Assignee: Labomatic Instruments, Allschwil, Switzerland

[21] Appl. No.: 448,625

[22] PCT Filed: Oct. 19, 1994

[86] PCT No.: PCT/CH94/00208

§ 371 Date: Jun. 6, 1995

§ 102(e) Date: Jun. 6, 1995

[87] PCT Pub. No.: WO95/11452

PCT Pub. Date: Apr. 27, 1995

[30] Foreign Application Priority Data

Oct. 19, 1993 [EP] European Pat. Off. ............ 93810734

[51] Int. Cl.⁶ .................................................. B01D 15/08
[52] U.S. Cl. ...................... 422/70; 422/102; 422/101; 210/198.2
[58] Field of Search ............................ 422/101–102, 422/68.1, 70; 210/198.2

[56] References Cited

U.S. PATENT DOCUMENTS

| 3,770,592 | 11/1973 | Noirot ............................ 422/101 |
| 4,597,866 | 7/1986 | Couillard . |

FOREIGN PATENT DOCUMENTS

| 0040663 | 12/1981 | European Pat. Off. . |
| 0041608 | 12/1981 | European Pat. Off. . |
| 0049850 | 4/1982 | European Pat. Off. . |
| 0460409 | 12/1991 | European Pat. Off. . |
| 63062506 | 8/1988 | Japan . |

*Primary Examiner*—Lyle A. Alexander
*Attorney, Agent, or Firm*—Anderson Kill & Olick P.C.

[57] ABSTRACT

The apparatus comprises a device connected to a closure body (10) in order to apply pressure to a packing in a chromatography column and a energy accumulator (11) which is in effective connection with the device in order to maintain the pressure applied to the packing. The device is connected to a column (2) to form an apparatus for chromatography. The apparatus is characterized by its broad field of use and its simple handling.

9 Claims, 1 Drawing Sheet

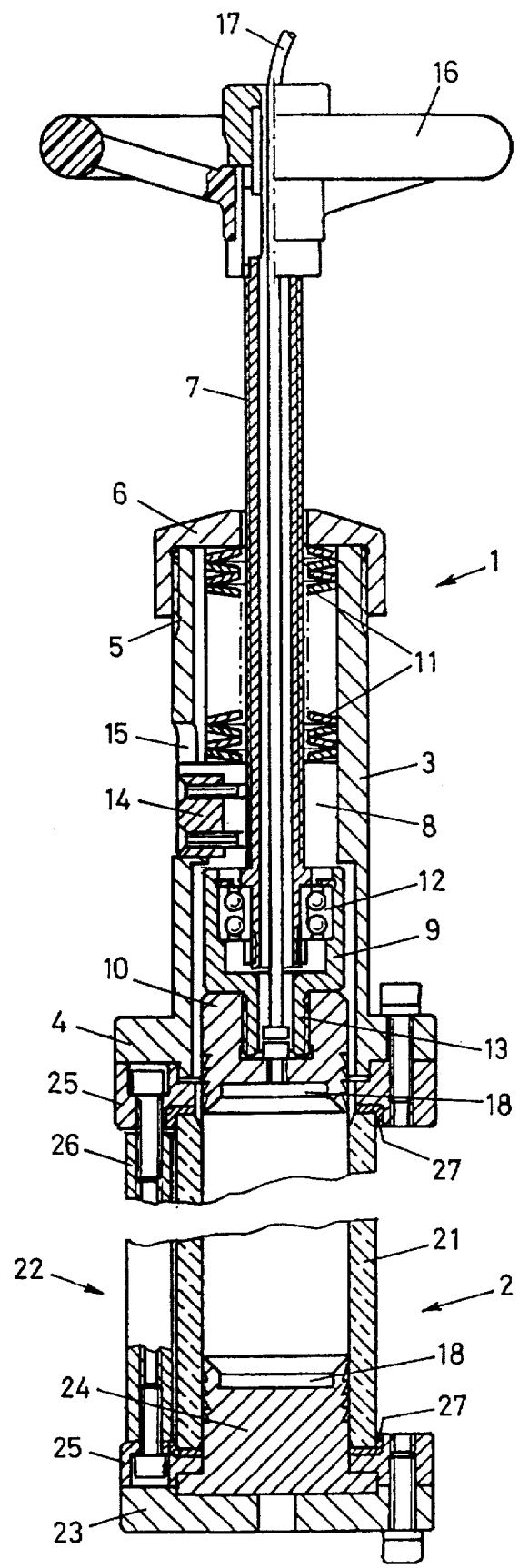

AXIALLY COMPRESSIBLE DEVICE FOR CHROMATOGRAPHY

The invention relates to a device for axially compressing a column for chromatography in accordance with the preamble of claim 1 as well as to an apparatus for chromatography having a device of this kind.

The object of the invention is to provide an apparatus for axially compressing a column for chromatography with which the pressure to be brought to bear on a column packing is produced by mechanical means and is maintained by a energy accumulator.

This object is satisfied in accordance with the invention by the characterizing features of claim 1.

The advantages achievable with the invention are eventually to be seen in the fact that the energy accumulator automatically compensates for height differences in the packing and that existing columns can be converted in a simple manner for use with the apparatus.

An apparatus for chromatography is characterized in accordance with the invention by the features of claim 12.

In this apparatus, it is advantageous that, in order to pack up the column after withdrawing the closure body, one only has to take off the device and that, in order to expel the used up packing from the column, the closure body need only be removed and the packing subsequently ejected by the device.

The invention will be described in the following by means of example only with the aid of the accompanying drawing which shows a section through an embodiment of an apparatus for chromatography in accordance with the invention together with an embodiment of a device in accordance with the invention for the axial compression of the column.

BRIEF DESCRIPTION OF THE DRAWING

As the FIGURE shows, the apparatus essentially comprises an apparatus 1 for the axial compression of a column for chromatography and a column 2 of this kind.

The device 1 comprises a cylinder-shaped housing 3 having a flange 4 at one end and an outer thread 5 at the other end. The device 1 further comprises a cover 6 which has a through-hole and which closes off the housing 3 on one side. The device further comprises screw drive with a threaded spindle 7 which passes through the cover and a member 8 which is screwed onto the threaded spindle and contacts the inner side of the housing with its periphery. The device also includes a plunger 9 rotatably mounted at one end of the threaded spindle 7, a closure body 10 which is connected to the plunger 9 and a energy accumulator made of disc springs 11.

The plunger 9 is journalled on the threaded spindle 7 by means of a roller bearing 12 and has a threaded projection 13 onto which the closure body 10 is screwed. The member 8 is arranged in the housing 3 so as to be fixed against rotation. For this, a part 14 is provided which, on the one hand, is connected to the member 8 and, on the other hand, is guided in a slot 15 formed in the wall of the housing. This part forms an indicator means for the pressure loading of the packing in the column. The energy acculator 11 is arranged between the member 8 and the cover 6 of the housing.

The threaded spindle 7 is a hollow spindle and is provided at its other end with a hand wheel 16. In this regard, it is noted that a pneumatic, hydraulic or electrical device can be used for driving the threaded spindle 7. With a drive device of this kind and a sensor device (not shown) which is in effective connection with the indicator part 14, it is possible to effect a pressure adjustment via a control device (not shown). Depending on the requirements, a pressure control loop can be provided in the control device. A feedline 17 is guided through the threaded spindle 7 to the closure body 10 and opens out into a filter unit 18. In this regard, it is noted that a like filter unit 18 is arranged in the closure body or terminal member 24. The filter unit 18 may be formed of a sintered body. Alternatively, the filter unit 18 may include two members formed of glass, ceramic, metal, plastic or the like.

The column 2 comprises a tube 21 made of glass and a holder device 22 for the tube, whereby a constructional unit is formed. The column further comprises a closure body 24 which closes off the tube at one end and a closure flange 23 which holds the closure body on the tube. The holder device comprises two flanges 25 and three tie rods 26. The flanges contact on either end face of the tube 21 and are held on the tube by means of tie rods. A plastic ring 27 is arranged between the tube and each flange in order to protect the tube against damage from the steel flanges.

The FIGURE shows the device in the non-pressurized state in which the device 1 can be separated from the column 2, with the closure body 10 being removed together with the device. With this arrangement of the closure body 10 relative to the device in accordance with the invention there is the advantage that the packing can be introduced into the column in a simple manner.

As can be seen from the FIGURE, the device 1 is mounted on the column 2 after the introduction of the packing that the column 2 is then closed off. By rotating the threaded spindle 7, the closure body 10 is displaced towards the packing. A rotation of the closure body is prevented by the plunger 9 which is arranged in a rotatable manner on the threaded spindle 7. In order to ensure this, a device providing security against rotation can be provided. If the closure body 10 lies on the packing, the packing is pressurized and compressed. Depending on the degree of density of the packing in the column, the member 8 is displaced towards the energy accumulator 11 by the rotation of the threaded spindle 7 and the disc springs are pressed together until the indicator part 14 contacts the end of the slot 15. In this position, the packing is subjected to the maximum pressure which can be maintained by means of the energy accumulator 11. Since the packing is compressed under the influence of the pressure exerted by the energy accumulator, the energy accumulator 11 expands. The value of the pressure reduction is indicated by the indicator part 14 which is displaced towards the column. If the pressure reduction reaches a particular value, the pressure on the packing inside the column can be increased once again by rotating the threaded spindle 7.

It should be added that the closure bodies 10, 24 of the invention are self-sealing. In the embodiment described, the closure bodies are sealed relative to the tube 21 by means of lip seals.

Instead of disc springs 11, other resilient members can be used in accordance with the invention for example rubber ones, pressure springs or the like.

We claim:

1. A device for applying axial pressure to a packing provided in a chromatographic column, said device comprising:
    a closure body displaceable in the column for applying axial pressure to the packing;
    means for displacing said closure body;
    an energy accumulator for maintaining the pressure applied to the packing wherein said energy accumulator comprises disc spring means; and means for actuating said energy accumulator in response to a predetermined axial pressure being applied to the packing,
   wherein said displacing means comprises a threaded spindle operationally connected with said closure body for displacing same, and
   wherein said actuating means comprises a nut screwed on said threaded spindle and displaceable against said energy accumulator upon the predetermined pressure being applied to the packing.

2. A device according to claim 1, wherein said threaded spindle has an end secured to the closure body.

3. A device according to claim 1, wherein said device further comprises a housing having an open end at which said housing is mountable on the column, said closure body and said energy accumulator being located in said housing.

4. An apparatus according to claim 1, further comprising drive means for rotating said threaded spindle.

5. An apparatus according to claim 1, further comprising means for preventing rotation of said nut during axial displacement of said threaded spindle, said preventing means comprising a member for indicating the pressure applied to the packing and connected with said nut.

6. An apparatus according to claim 1, wherein said closure body comprises a filter unit.

7. An apparatus according to claim 6, wherein said filter unit comprises a sintered body.

8. An apparatus according to claim 6, wherein said filter unit comprises at least two members formed of a material selected from a group consisting of glass, ceramic, metal and plastic.

9. A device according to claim 6, wherein said threaded spindle is hollow, and wherein said device comprises a feed line extending through said threaded spindle and opening into said filter until.

* * * * *